United States Patent
Rubin

(10) Patent No.: US 6,846,942 B2
(45) Date of Patent: Jan. 25, 2005

(54) METHOD FOR PREPARING PURE EPA AND PURE DHA

(76) Inventor: David Rubin, 8949 Montrose Way, San Diego, CA (US) 92122

( * ) Notice: Subject to any disclaimer, the term of this patent is extended or adjusted under 35 U.S.C. 154(b) by 36 days.

(21) Appl. No.: 10/441,266

(22) Filed: May 20, 2003

(65) Prior Publication Data

US 2004/0236128 A1 Nov. 25, 2004

(51) Int. Cl.$^7$ .................................................. C11B 7/00
(52) U.S. Cl. ........................ 554/195; 554/198; 554/206; 554/208; 554/211
(58) Field of Search ............................... 554/195, 198, 554/206, 208, 211

(56) References Cited

U.S. PATENT DOCUMENTS

| | | |
|---|---|---|
| 4,792,418 A | 12/1988 | Rubin et al. |
| 4,961,936 A | 10/1990 | Rubin |
| 5,006,281 A | 4/1991 | Rubin et al. |
| 5,013,569 A | 5/1991 | Rubin |
| 5,130,061 A | 7/1992 | Cornieri et al. |
| 5,336,792 A | 8/1994 | Sola et al. |
| 5,518,918 A | 5/1996 | Barclay |
| 6,020,020 A | 2/2000 | Cain et al. |
| 6,159,523 A | 12/2000 | Cain et al. |
| 6,190,715 B1 | 2/2001 | Crowther et al. |
| 6,235,331 B1 | 5/2001 | Kataoka et al. |
| 6,395,778 B1 | 5/2002 | Luthria |
| 6,451,567 B1 | 9/2002 | Barclay |

FOREIGN PATENT DOCUMENTS

| | | |
|---|---|---|
| GB | 2033745 A | 5/1980 |
| GB | 2148713 A | 10/1984 |

OTHER PUBLICATIONS

Gonzalez et al., "Optimization of Fatty Acid extraction from Phaeodactylum tricornutum UTEX 640 biomass", JAOCS, vol. 75, No. 12, pp. 1735–1740, 1998.*

* cited by examiner

Primary Examiner—Deborah D. Carr
(74) Attorney, Agent, or Firm—Browdy and Neimark, P.L.L.C.

(57) ABSTRACT

Pure DHA and pure EPA can be obtained from a mixture of EPA and DHA in a solution by forming salts of DHA and EPA which have different solubilities in the solvent, cooling the solution until the salt of EPA is formed, filtering the solution to recover the salt of EPA, and acidifying the EPA salt and the DHA salt to obtain pure EPA and pure DHA.

9 Claims, No Drawings

METHOD FOR PREPARING PURE EPA AND PURE DHA

FIELD OF THE INVENTION

The present invention relates to methods for obtaining pure EPA and pure DHA from natural sources.

BACKGROUND OF THE INVENTION

Various fats and fatty oils comprise triglycerides of fatty acids. Many fatty acids, particularly polyunsaturated fatty acids, are difficult to synthesize and can only be obtained by extraction from natural fats or fatty oils in which they naturally occur. Many of these unsaturated fatty acids are known to be valuable for their therapeutic properties. Others are thought to have undesirable effects. Furthermore, the fatty acids having therapeutic properties must be in a particular cis-trans isomeric form. There has long been a need for obtaining individual unsaturated fatty acids in pure form and high quantity, without cis-trans conversion.

Two particular polyunsaturated fatty acids which have been shown to have therapeutic efficacy, and which are difficult to obtain in pure form and large quantities, are (all-Z)-5,8,11,14,17-eicosapentaenoic acid, hereinafter referred to as EPA, and (all-Z)-4,7,10,13,16,19-docosahexaenoic acid, hereafter referred to as DHA. Both EPA and DHA are known to be precursors in the biosynthesis of prostaglandin PGE3.

It is well known that ω-3 fatty acids, such as EPA and DRA, are useful dietary compounds for preventing arteriosclerosis and coronary heart disease, for alleviating inflammatory conditions, and for retarding the growth of tumor cells. Recently, DHA has been the focus of attention because this polyunsaturated fatty acid is the major fatty acid that occurs in the brain and the retina. Also, DHA is the only member of the ω-3 fatty acids that occurs naturally in mother's milk.

British Patents Nos. 1,604,554 and 2,033,745, disclose the use of ω-3 fatty acids for treating thromboembolic conditions. British patent No. 2,148,713, to the present inventor, also discloses the use of EPA and/or DHA, in combination with other fatty acids, for reduction of serum cholesterol and triglyceride levels.

It has heretofore been very difficult to obtain pure EPA and DHA, since the main source of these fatty acids is in the fats and oils of marine animals, fish oils (such as mackerel oil, menhaden oil, salmon oil, capelin oil, tuna oil, sardine oil, or cod oil), marine algae such as Schizochytrium sp., human milk, and vegetable oils, such as linseed oil, either as itself or in the form of a derivative such as a triglyceride. It is difficult to obtain pure DHA or EPA, because these sources normally contain a substantial amount of fatty acid residues, often as residues of triglyceride molecules, which dilute the concentration of DHA or EPA in the oil. Other fatty acids are always present in larger amounts. Since EPA and DHA are known to be medically effective for treating a variety of conditions, highly pure EPA and DHA are required in large amounts to conduct clinical studies and for therapy.

The beneficial effects of ω-3 fatty acids result both from competitive inhibition of compounds produced from ω-6 fatty acids, and from beneficial compounds produced directly from the ω-3 fatty acids themselves. Ω-6 fatty acids are the predominant fatty acids found in plants and animals. Most commercially available ω-3 fatty acids are obtained from certain fish oils, which contain up to 20–30% of these fatty acids. Consequently, large quantities of fish oil are processed and encapsulated each year for sale as a dietary supplement. However, there are several significant problems with these fish oil supplements, including bioaccumulation of fat-soluble vitamins and high levels of saturated and ω-6 fatty acids, both of which can have deleterious health effects.

Previous methods for extracting EPA, DHA and other useful polyunsaturated fatty acids from their triglycerides have not been satisfactory for producing highly pure fatty acids. The term "purity" is used here to mean not only in the sense of being separated from all other fatty acids of different chain lengths, and different number and placement of unsaturation, but also the purity of the particular cis-trans structure. Prior methods not only did not yield sufficient purity, but in many cases also required such extreme physical and chemical conditions as to cause some degree of degradation of the fatty acids, formation of peroxides, and/or conversion of some of the cis- bonds to the trans-form. Furthermore, many prior art processes use materials which are not on the Generally Recognized as Safe (GRAS) list of the U.S. Food and Drug Administration. In order for the final product to be used in foods and drugs, it is important that there be no nonGRAS substances in the final product.

Fujita et al., in U.S. Pat. No. 4,377,526, disclose one method for purifying EPA. In this patent, a mixture of fatty acids containing EPA is treated with urea in order to remove saturated fatty acids and fatty acids of lower unsaturation. The resultant solution is then subjected to fractional distillation in order to obtain higher yields of EPA. The fractional distillation, however, requires a temperature of at least 180° C. over a period of at least 40 minutes. The best purity which can be obtained by this method set forth in any of the examples is 92.9%. Furthermore, it has been discovered that a substantial amount of the EPA produced by this method, in some cases as much as 20%, has some degree of cis-trans conversion. Any amount of the trans-form of EPA is strictly undesirable for food or pharmaceutical use.

Abu-Nasr et al., *J. Am. Oil Chemists Soc.* 31, 41–45 (1954) disclose isolation of methyl eicosapentaenoate and ethyl docosahexaenoate using cod liver oil acids, using preliminary concentration by precipitation of the pure complexes followed by chromatographic separations. This technique does not give high enough purity, and chromatographic separations require undesirably high amounts of solvent.

Teshima et al., in *Bulletin of the Japanese Society of Scientific Fisheries,* 44(8) 927 (1978) describe a method for isolating EPA and DHA from squid liver oil by saponifying with ethanolic potassium hydroxide, extracting the fatty acids with ether, and methylating. The crude fatty acid methyl ester is purified by column chromatography on Silica Gel 60, and then the EPA is separated from the DHA by column chromatography on a mixture of silver nitrate and silica gel. The problem with this technique is that there are often traces of silver left in the final product, which is extremely undesirable in a food or pharmaceutical for human consumption. Furthermore, very high amounts of solvent are necessary to conduct the column chromatography.

Other disclosures of the use of column chromatography to separate and purify EPA to some extent are described in Japanese Kokai No. 56, -115736 and Russian No. 973,128.

Rubin, in British Patent No. 2,148,713, describes a process in which the double bonds of the unsaturated fatty acids, in a mixture of fatty acids, are iodinated, followed by saponification of the iodinated oil, extraction of the fatty acids from the saponification mixture, methylation of the iodinated fatty acids, separation of the fatty acids by column chromatography, and then deiodination of the desired fractions. This process permits excellent resolution of the fatty acids upon eventual column chromatography, and protects the fatty acids from oxidation during processing. When used to separate EPA from a natural source of EPA, such as cod liver oil, a yield of over 90% and a purity of 96–100% may be obtained. It has been found, however, that a substantial amount of cis-trans conversion occurs in the course of this process, so that the product obtained is not pure all-cis EPA. Furthermore, iodine is not on the list of GRAS materials.

Rubin, in U.S. Pat. No. 4,792,418, describes a process for obtaining pure polyunsaturated fatty acids such as EPA and DHA and their esters, without degradation thereof. This process involves first hydrolyzing the triglycerides of the oil source under mild conditions, as with lipase, removing non-saponifiable material by washing with organic solvent, treating with urea in order to remove saturated and monounsaturated fatty acids to form a urea complex with saturated and mono-saturated fatty acids, dissolving the remainder in an organic solvent, preferably acetone, slowly cooling and fractionally removing solidified material as it forms.

Barclay, in U.S. Pat. Nos. 5,518,918, and 6,451,567, discloses production of ω-3 fatty acids by growing Thraustochytrium, Schizochytrium, and mixtures thereof with high ω-e3 fatty acid content in a fermentation medium. However, this process produces a mixture of ω-3 fatty acids, rather than individual ω-3 fatty acids.

Best et al., in U.S. Pat. No. 5,928,696, extract oils from native substances using centrifugation. Again, this method produces mixtures of unsaturated fatty acids rather than pure individual fatty acids.

Kyle et al., in U.S. Pat. No. 5,397,591, disclose a method for obtaining DHA from cultivation of dinoflagellates in a fermentor, induction of the dinoflagellates to produce single cell oil having a high proportion of DHA, and recovery of that oil. Preferably, the oil recovered contains at least about 20% by weight of DHA, and more preferably, more than about 35% by weight DHA. The product recovered is not pure DHA, but a mixture of DHA in other oils.

Cornieri et al., in U.S. Pat. No. 5,130,061, disclose a process for extracting polyunsaturated fatty acid esters from fish oils. However, the product obtained is a mixture of EPA and DHA esters.

SUMMARY OF THE INVENTION

It is an object of the present invention to avoid the aforesaid deficiencies in the prior art.

It is another object of the present invention to obtain pure EPA and DHA in a simple procedure.

It is another object of the present invention to obtain pure EPA and DHA without any cis-trans conversion.

According to the present invention, fish oil is saponified with a base to which is added a small amount of ethanol to start the reaction. The mixture is stirred under nitrogen in a cool bath. Then, a solvent such as methylene chloride or ethylene chloride is added and stirred vigorously. The mixture is poured into a separating funnel. The methylene chloride phase is removed to remove unsaponified materials. Free fatty acids are obtained from their sodium salts by adding an acid such as acetic acid. The saturated fatty acids are removed by adding a solvent such as diethyl ether or acetone, and refrigerating the mixture to solidify the saturated fatty acids to ease in their removal.

To obtain 100% ω-3 fatty acids, a base such as sodium hydroxide in ethanol is added to the acetone solution. Any other suitable base can be used, but preferably the base is GRAS listed. After refrigeration at –20° C., the solids formed are removed, leaving in the solution substantially only EPA and DHA. The acetone is evaporated and collected. Water is added and titrated with 50% acetic acid to convert the sodium salts to free EPA and DHA.

To separate DHA from EPA, magnesium salts of the acids are formed. Surprisingly, the magnesium salt of DHA is much more soluble in acetone than the magnesium salt of EPA. The difference in solubility is greater the lower the temperature of the acetone.

DETAILED DESCRIPTION OF THE INVENTION

The essential feature of the present invention is that EPA can be separated from DHA by forming magnesium salts, and separating the magnesium salts on the basis of their solubility in a solvent such as acetone. This method of separation of EPA and DHA avoids any extreme conditions throughout the procedure, which helps to avoid any cis-trans conversion.

The oil from which the EPA and DHA are obtained by means of the present invention is preferably as fresh as possible so that the separation maybe effected before any substantial degradation of the fatty acids occurs. Natural fats or oils containing high levels of EPA and DHA suitable for use in the present invention include, for example, fats and oils of marine animals such as blue-colored fish, such as mackerel, sardines, mackerel pike, and herring; cod liver oil; and animal marine plankton such as krill and the various shrimp-like copepods. It should be understood, however, that any source of EPA and DHA may be used in the present invention. Preferably, the source fish are obtained from as cold an environment as possible. The optimal enzymatic activity for the enzyme δ-5-desaturase, which catalyzes the conversion of eicosatetraenoic acid to EPA, occurs at 9° C. Thus, fish from cold environments are higher in EPA than are fish from warmer waters.

Furthermore, even greater yields of EPA can be obtained if the fish are raised in a controlled environment. If the fish are fed a diet rich in α-linolenic acid and maintained in salt water at 9° C., optimum amounts of EPA will be produced.

The natural fat or oil is subjected to saponification or alcoholysis in order to convert the triglycerides to free fatty acids or esters of fatty acids. The method selected, however, should be one which avoids high temperatures and strongly basic reagents, as these can lead to peroxidation and cis-trans conversion. The preferred method of hydrolysis is enzymatic hydrolysis using the enzyme lipase at a temperature of about 35–40° C. and a pH of about 6–7. The lipase should be activated by traces of cysteine or ascorbic acid, as is conventional. Another advantage of the use of lipase for saponification is the fact that lipase enzyme, being steroespecific, will not cleave any trans-fatty acids, which may be produced in nature from the triglycerides. Thus, even if there is a trans-EPA or DHA in the starting material, it will be removed with the non-saponified materiel and will not be present in the final product.

An alternative method for hydrolyzing the natural fats and oils is by partially hydrolyzing these fats and oils with lipase or a strong base. When lipase is used, hydrolysis for 1.5 to 2 hours, rather than the usual six hours, provides a richer source of EPA because the lipase preferentially removes the first and third branches of the treated triglyceride. It is known that in natural triglycerides the outside branches have more greatly saturated chains than the middle branch. Thus, limiting the amount of hydrolysis automatically removes a substantial amount of the more saturated acids.

A base such as potassium hydroxide or sodium hydroxide can also be used to partially hydrolyze the natural fats or oils. The source of oil is treated with the base for about 15–20 minutes to partially hydrolyze the triglycerides. As in the case with lipase, this partial hydrolysis yields a richer source of EPA from the triglyceride the first and third branches of the triglycerides are preferentially attacked by the base.

After the hydrolysis step, unsaponified materials are removed with an organic nonpolar solvent such as methylene chloride, petroleum ether, ethyl ether, etc. The organic solvent removes cholesterol, PCB's and other non-saponified materials, including vitamins A and D and hydrocarbons. This procedure is repeated several times until the desired purity is reached.

Next, free fatty acids are formed from the sodium salt by acidifying the aqueous phase. Any acid can be used for this step, although pharmaceutically acceptable acids such as acetic acid are preferred. This acidification will cause the free fatty acids to separate into a separate organic phase. The aqueous phase is then discarded. Adding a small amount of a salt such as sodium chloride will enhance the separation.

The organic phase, containing the free fatty acids, is then dissolved in acetone and refrigerated at about −20° C. overnight. The saturated fatty acids solidify and can be removed by filtering.

To obtain 100% α-3 fatty acids from the acetone solution, a mixture of a base such as sodium hydroxide and ethanol is added. This mixture is left overnight under refrigeration at about −20° C. The acetone is evaporated and collected for future use.

The above three steps are repeated three times. Each time the amount of water is about 50% less than the time before. The solution obtained consists of essentially 100% ω-3 fatty acids. These free fatty acids can be protected by adding a conventional, pharmaceutically acceptable or food-grade antioxidant, such as ascorbyl palmitate or γ-tocopherol.

DHA and EPA can be separated from each other by forming salts of the acids which have different solubilities. For example, the magnesium salts of these acids have different solubilities in acetone, particular at sub-zero temperatures. The salts are formed by adding a salt of the cation to be used in acetone to the above-described 100% α-3 preparation. The solution is left overnight under refrigeration at about −20° C. The EPA salt, which is less soluble in acetone than the DHA salt, precipitates as white flakes. These white flakes are filtered out and reconstituted from the salt by acidifying. The DHA salt remains in solution, and the DHA can be obtained by acidifying the solution and recovering the free DHA by conventional means.

Pure Ω-3 fatty acids can be obtained based upon the difference in solubility in acetone of the magnesium or other group II metal salts that are soluble in acetone salts of the fatty acids.

While the present process has been described with respect to the use of acetone as the organic solvent from which the fatty acid EPA salt is precipitated upon cooling, it should be understood that any other organic solvent can be used for this purpose as long as the relative precipitation points of the EPA and DHA salts are far enough from one another that pure precipitate can be separated. It is believed that from most solvents the temperature of precipitation of the salts is independent of the particular solvent used, although it depends upon concentration of the fatty acid in the solvent.

Whether any given solvent is operable or inoperable for separation of salts of EPA and DHA can readily be determined by routine experimentation. The preferred organic solvents are those which are non-toxic and generally recognized as safe, or which can be completely eliminated without substantial treatment. Furthermore, it is necessary that the solvent remain in the liquid state throughout the range of temperatures of precipitation of the EPA salts, depending upon the concentration of the EPA salt, for example, to a temperature of at least −70° C.

The precise temperatures to which the solutions are cooled to separate EPA from DHA, and the precise amounts of volume reduction, will differ depending upon the particular EPA and DHA salts and the particular solvent. These parameters can be empirically determined by those skilled in the art without undue experimentation. The solution may be cooled to a temperature slightly below that at which precipitation begins, and maintained at that temperature until precipitation is completed.

The present invention is illustrated by the following non-limiting example:

EXAMPLE

1. Saponification

One kilogram of fish oil was mixed with a solution of 260 grams potassium hydroxide. Ten mL of ethanol was added to start the reaction. The mixture was vigorously mixed under nitrogen for one hour in a cool bath (temperature should not exceed about 40° C.).

2. Removal of Unsaponified Materials

One hundred mL of methylene chloride was added and the mixture was stirred vigorously. The mixture was poured into a separating funnel and the methylene chloride phase was removed (carrying with it cholesterol, PCB's and other non-saponified materials). This procedure was repeated several times until the desired purity was reached. Purity was determined by micro analysis.

3. Formation of Free Fatty Acids from their Sodium Salts

Four liters of 50% acetic acid was mixed vigorously with the mixture obtained from the methylene chloride separation. For acidification, any non-oxidizing can be used. The water phase, which contained sodium acetate, was removed, and the organic phase was washed three times.

4. Removal of the Saturated Fatty Acids

Twenty liters of acetone was added. The solution was left in a refrigerator at −20° C. overnight. The saturated fatty acids solidified and were removed.

5. Separation of 100% Ω-3 Fatty Acids

One hundred grams of sodium hydroxide was dissolved in one liter of water, and two liters of ethanol were added. The sodium solution was mixed with the acetone solution of the fatty acids and was left overnight in the refrigerator at about −20° C. The acetone was evaporated in a roto evaporator and collected for a future reaction. Step 3 was repeated using only one liter of 50% acetic acid solution.

The resulting preparation consists essentially of 100% α-3 fatty acids. Ascorbyl palmitate or y-tocopherol, 1 ppm, are the preferred antioxidants for protecting this product.

Separating EPA from DEA

It was surprisingly discovered that the magnesium salts of EPA and DHA have different solubilities in acetone. When the magnesium salts of a mixture of EPA and DHA were dissolved in acetone, it was found that the magnesium salt of DHA was much more soluble in acetone than the magnesium salt of EPA. This solubility difference was even greater at sub-zero temperatures.

Fifty grams of magnesium acetate was dissolved in one liter of acetone. One hundred mL of the above-described Ω-e preparation was mixed in the magnesium-acetone solution and stirred vigorously. The solution was left overnight in the refrigerator at −20° C. A white precipitate formed, which was discovered to be more than 95% EPA, iodine value 384.2. After the solution was reconstituted, a product of more than 95% DHA was recovered, iodine value 402.1.

Both the EPA and DHA obtained from this process are sufficiently pure for pharmaceutical or food use.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

What is claimed is:

1. A method for separating free EPA from a mixture of EPA and DHA comprising:
    a. dissolving the mixture of EPA and DHA in a solvent and adding a salt of a metal ion that produces salts of EPA and DHA which have different solubilities in the solvent;
    b. cooling the solution obtained in step (a) to precipitate the salt of EPA from solution;
    c. filtering the solution to remove the EPA salt; and
    d. acidifying the precipitate obtained from filtering the solution to produce pure EPA.

2. The method according to claim 1 wherein the metal ion is magnesium.

3. The method according to claim 1 wherein the solvent is acetone.

4. The method according to claim 1 wherein after the EPA salt has been filtered from the solution, the solvent is evaporated to recover DHA salt, and the DHA salt is acidified to produce pure DHA.

5. A method for obtaining substantially pure EPA and DHA from a naturally occurring fat or oil comprising:
    a. subjecting the natural fat or oil to saponification or alcoholysis to convert triglycerides to free fatty acids;
    b. removing unsaponified materials with an organic nonpolar solvent;
    c. add an acid to the nonpolar solvent solution to form free fatty acids;
    d. dissolve the solution in acetone and refrigerate the solution to precipitate saturated fatty acids;
    e. add a base to the solution;
    f. evaporate the acetone to produce a solution of ω-3 fatty acids;
    g. adding a salt which forms salts with ω-3 fatty acids which have differing solubilities in acetone;
    h. refrigerating the solution to case the EPA salt to precipitate;
    i. acidify the solution to obtain free DHA;
    j. acidifying the EPA salt to produce free EPA.

6. The method according to claim 5 wherein the natural oils are hydrolyzed with lipase.

7. The method according to claim 5 wherein the natural oils are saponified by adding a base.

8. The method according to claim 7 wherein the base is NaOH or KOH.

9. The method according to claim 5 wherein the nonpolar solvent is methylene chloride.

* * * * *